US009180433B2

(12) United States Patent
Wang et al.

(10) Patent No.: US 9,180,433 B2
(45) Date of Patent: Nov. 10, 2015

(54) CATALYSTS FOR 2-CHLORO-1,1,1,2-TETRAFLUOROPROPANE DEHYDROCHLORINATION

(71) Applicant: HONEYWELL INTERNATIONAL INC., Morristown, NJ (US)

(72) Inventors: Haiyou Wang, Amherst, NY (US); Hsueh Sung Tung, Getzville, NY (US)

(73) Assignee: HONEYWELL INTERNATIONAL, INC., Morrristown, NJ (US)

( * ) Notice: Subject to any disclaimer, the term of this patent is extended or adjusted under 35 U.S.C. 154(b) by 57 days.

(21) Appl. No.: 14/206,587

(22) Filed: Mar. 12, 2014

(65) Prior Publication Data

US 2014/0275649 A1    Sep. 18, 2014

Related U.S. Application Data

(60) Provisional application No. 61/783,835, filed on Mar. 14, 2013.

(51) Int. Cl.

| *B01J 23/58* | (2006.01) |
|---|---|
| *C07C 17/25* | (2006.01) |
| *C07C 17/087* | (2006.01) |
| *C07C 17/20* | (2006.01) |
| *B01J 21/10* | (2006.01) |
| *B01J 37/02* | (2006.01) |
| *B01J 23/44* | (2006.01) |

(52) U.S. Cl.
CPC *B01J 23/58* (2013.01); *B01J 21/10* (2013.01); *B01J 37/0201* (2013.01); *C07C 17/087* (2013.01); *C07C 17/206* (2013.01); *C07C 17/25* (2013.01); *B01J 23/44* (2013.01)

(58) Field of Classification Search
CPC ........................................................ B01J 23/58

USPC .......................................................... 502/328
See application file for complete search history.

(56) References Cited

U.S. PATENT DOCUMENTS

| 5,068,473 | A  | 11/1991 | Kellner et al. |
|---|---|---|---|
| 7,829,748 | B1 | 11/2010 | Tung et al. |
| 8,263,817 | B2 | 9/2012 | Nappa et al. |
| 2005/0020862 | A1 | 1/2005 | Tung et al. |
| 2007/0197842 | A1 | 8/2007 | Mukhopadhyay et al. |
| 2009/0240090 | A1 | 9/2009 | Merkel et al. |
| 2009/0299107 | A1 | 12/2009 | Wang et al. |
| 2010/0191024 | A1 | 7/2010 | Uenveren et al. |
| 2011/0060172 | A1 | 3/2011 | Wang et al. |
| 2011/0270000 | A1 | 11/2011 | Bektesevic et al. |
| 2011/0282111 | A1 | 11/2011 | Wang et al. |
| 2012/0108859 | A1 | 5/2012 | Nappa et al. |
| 2012/0129687 | A1 | 5/2012 | Wang et al. |

FOREIGN PATENT DOCUMENTS

| WO | WO2009009421 A1 | 1/2009 |
|---|---|---|
| WO | 2012057367 A1 | 5/2012 |

OTHER PUBLICATIONS

E Ruckenstein, et al., "Effect of Calcination conditions on the species formed and the reduction behavior of the cobalt-magnesia catalysts"; Catalysis Letters 70 (2000) pp. 15-21.
International Search Report and Written Opinion issued in International Application No. PCT/US2014/025243 dated Jul. 1, 2014.

*Primary Examiner* — Edward Johnson
(74) *Attorney, Agent, or Firm* — Scully, Scott, Murphy & Presser, P.C.

(57) ABSTRACT

The present invention relates to a provides a catalyst comprising (a) a solid support comprising an alkaline earth metal oxide, fluoride, or oxyfluoride, and (b) at least one elemental metal disposed on or within said support, preferably wherein said elemental metal is present in an amount from about 0.01 to about 10 weight percent based upon the total weight of the metal and support. It also relates to the use of the catalyst for the dehydrochlorination of a hydrochlorofluorocarbon.

47 Claims, No Drawings

CATALYSTS FOR 2-CHLORO-1,1,1,2-TETRAFLUOROPROPANE DEHYDROCHLORINATION

FIELD OF THE INVENTION

The present invention relates to catalysts useful for the dehydrohalogenation of a halogen-containing compound and to the use of these catalysts for the dehydrohalogenation of a halogen-containing compound. For example, the present invention relates to catalysts for the dehydrochlorination of a hydrochlorofluorocarbon to form a fluorinated olefin, and to the use thereof for the dehydrochlorination of a hydrochlorofluorocarbon to a fluorinated olefin. In another instance, the present invention further relates to catalysts for the dehydrochlorination of 2-chloro-1,1,1,2-tetrafluoropropane to 2,3,3,3-tetrafluoropropene and to the use thereof for the dehydrochlorination of 2-chloro-1,1,1,2-tetrafluoropropane to 2,3,3,3-tetrafluoropropene.

BACKGROUND

Chlorine-containing compounds, such as chlorofluorocarbons (CFCs), have been employed as refrigerants, foam blowing agents, cleaning agents, solvents, heat transfer media, sterilants, aerosol propellants, dielectrics, fire extinguishing agents, and power cycle working fluids. However, CFCs have proven to be detrimental to the Earth's ozone layer. Conventional substitutes for CFCs include hydrofluorocarbons (HFCs); however, these compounds have been found to contribute to global warming. For these reasons, there is a worldwide effort to develop new compounds that are environmentally benign.

Partly or fully fluorinated olefins, including hydrofluoroolefins, (collectively referred to hereinafter as fluorinated olefins) are potential replacements for HFCs and CFCs. They can be used in some of the aforementioned applications and can also be used as feedstock monomers to synthesize fluoropolymers and other macromolecular compounds.

Various methods for producing certain fluorinated olefins are known, including those involving the dehydrochlorination of hydrochlorofluorocarbons. For example, U.S. patent application Ser. No. 11/619,592 discloses a method for preparing 2,3,3,3-tetrafluoropropene (1234yf) via dehydrochlorination of 2-chloro-1,1,1,2-tetrafluoropropane (244bb) with the aid of a catalyst. The 244bb reactant can be prepared through liquid phase or gas phase catalytic fluorination of 1,1,1-trifluoro-2-chloropropene (1233xf) with HF and 1233xf, in turn, can be made via gas phase fluorination of $CCl_2=CCl—CH_2Cl$ (1,1,2,3-tetrachloropropene) with HF. The '592 application also teaches the use of a carbon- and/or metal-based catalyst for the conversion of 244bb to 1234yf. Depending on the reaction conditions, the conversion of 244bb could be as high as 98%, but it has selectivity for 1234yf of only 69% to 86%. Thus, there remains a need to develop a commercially viable catalyst that not only is active, but also is more selective for 1234yf.

However, the conversion of a hydrochlorofluorocarbon to a fluorinated olefin by conventional methods is problematic because by-products often form and compete in the dehydrofluorination reaction, thereby reducing the yield of the desired fluorinated olefin. Hence, it would be advantageous to develop a catalyst system that can suppress undesirable dehydrofluorination reactions, so that single-pass productivity and yield of the desired fluorinated olefin can be increased.

SUMMARY OF THE INVENTION

It has been found that metal catalysts supported on alkaline earth metal oxide, fluoride, or oxyfluoride provide high activity and selectivity for the dehydrochlorination of a hydrochlorofluorocarbon.

Accordingly, one aspect of the invention described herein provides a catalyst comprising (a) a solid support comprising an alkaline earth metal oxide, fluoride, or oxyfluoride, and (b) at least one elemental metal disposed on or within said support, preferably wherein said elemental metal is present in an amount from about 0.01 to about 10 weight percent based upon the total weight of the metal and support. This catalyst is useful for dehydrohalogenating hydrochlorofluorocarbon.

Another aspect of the present invention is directed to a process of making 2,3,3,3-tetrafluoropropene (1234yf) via dehydrochlorination of 2-chloro-1,1,1,2-tetrafluoropropane (244bb) which comprises dehydrochlorinating 2-chloro-1,1,1,2-tetrafluoropropane with the catalyst described herein.

DETAILED DESCRIPTION OF THE INVENTION

Before addressing details of embodiments described below, some terms are defined or clarified.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B is true (or present).

Also, use of "a" or "an" is employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. In case of conflict, the present specification, including definitions, will control. Although methods and materials similar or equivalent to those described herein can be used in the practice or testing of embodiments of the present invention, suitable methods and materials are described below. In addition, the materials, methods, and examples are illustrative only and not intended to be limiting.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

As used herein, the term "alkaline earth metal" is defined as an element selected from beryllium, magnesium, calcium, strontium, or barium or combination thereof. In an aspect, the term "alkaline earth metal" refers to magnesium, calcium, strontium, or barium or combination thereof.

The term, "alkaline earth metal oxide", as used herein refers to oxides of alkaline earth metals, such as magnesium oxide, calcium oxide, strontium oxide, barium oxide or combination thereof.

The alkaline earth fluorides include, but are not limited to, magnesium fluoride, calcium fluoride, strontium fluoride, barium fluoride, or combination thereof.

The alkaline earth oxyfluorides include, but are not limited to, magnesium oxyfluoride, calcium oxyfluoride, strontium oxyfluoride, barium oxyfluoride or combination thereof.

The term "elemental metal", as used herein, refers to a metal selected from Group 7, 8, 9, 10, or 11 of the periodic table or combination thereof. Examples include Pd, Ru, Pt, Rh, Ir, Fe, Co, Ni, Cu, Ag, Re, Os and Au and any combination thereof.

The term "hydrochlorofluorocarbon" is a saturated alkane molecule containing carbon, hydrogen, and at least one chlorine atom on an adjacent carbon atom. Examples include $CF_3CFClCH_3$ (244bb), $CF_3CHFCH_2Cl$ (244eb), $CF_3CH_2CHFCl$ (244fa), $CF_3CHClCH_2F$ (244db), $CF_3CFClCH_2F$ (235bb), $CF_3CHFCHFCl$ (235ea), $CF_3CH_2CF_2Cl$ (235fa), $CF_3CHClCHF_2$ (235da), $CF_3CFClCHF_2$ (226ba), $CF_3CH_2CHCl_2$ (243fa), $CF_3CHClCH_2Cl$ (243db), $CF_3CCl_2CH_3$ (243ab), $CF_3CHFCHCl_2$ (234ea), $CF_3CFClCH_2Cl$ (234bb), $CF_3CHClCHCl_2$ (233da), $CF_3CCl_2CH_2Cl$ (233ab), and the like.

The term "fluoroolefin", as used herein, means a molecule containing hydrogen, carbon, fluorine, and a carbon-carbon double bond and optionally chlorine. Examples are described throughout the instant specification.

The term "hydrofluoroolefin", as used herein, means a molecule containing hydrogen, carbon, fluorine, and a carbon-carbon double bond.

The term "hydrochlorofluoroolefin", as used herein, means a molecule containing hydrogen, carbon, chlorine, fluorine, and a carbon-carbon double bond.

The term "dehydrohalogenation", as used herein, means dehydrofluorination or dehydrochlorination. The term "dehydrohalogenating", as used herein, means dehydrofluorinating or dehydrochlorinating. The term "dehydrohalogenated", as used herein, means dehydrofluorinated or dehydrochlorinated.

The term "dehydrofluorination", "dehydrofluorinating" or "dehydrofluorinated", as used herein, means a process during which hydrogen and fluorine on adjacent carbons in a molecule are removed.

The term "dehydrochlorination", "dehydrochlorinating", or "dehydrochlorinated", as used herein, means a process during which hydrogen and chlorine on adjacent carbons in a molecule are removed.

HFO-1234ze may exist as one of two configurational isomers, E or Z. HFO-1234ze as used herein refers to the isomers, E-HFO-1234ze or Z—HFO-1234ze, as well as any combinations or mixtures of such isomers.

HFO-1225ye may exist as one of two configurational isomers, E or Z. HFO-1225ye as used herein refers to the isomers, E-HFO-1234ze or Z—HFO-1225ye, as well as any combinations or mixtures of such isomers.

HCFO-1233zd also may exist as one of two configurational isomers, E or Z. HCFO-1233zd as used herein refers to the isomers, E-HCFO-1233zd or Z—HCFO-1233zd, as well as any combinations or mixtures of such isomers.

$CF_3CF{=}CHCl$ (HCFO-1224yd) also may exist as one of two configurational isomers, E or Z. HCFO-1224yd as used herein refers to the isomers, E-HCFO-1224yd or Z—HCFO-1224yd, as well as any combinations or mixtures of such isomers.

$CF_3CCl{=}CHCl$ (HCFO-1223xd) also may exist as one of two configurational isomers, E or Z. HCFO-1223xd as used herein refers to the isomers, E-HCFO-1223xd or Z—HCFO-1223xd, as well as any combinations or mixtures of such isomers.

An embodiment of the invention is directed to a catalyst comprising (a) a solid support impregnated with an alkaline earth metal oxide or alkaline earth oxyfluoride or alkaline earth fluoride or combination thereof and (b) at least one elemental metal, as defined herein, disposed on or within said support, said elemental metal being present in an amount from about 0.01 to about 10 wt %, based upon the total weight of the metal and support (including the alkaline earth metal oxide, fluoride and oxyfluoride). In an embodiment, the catalyst includes magnesium oxide, magnesium oxyfluoride or magnesium fluoride as the solid support and the elemental metal disposed on or within said support being a metal in group 7, 8, 9, 10, or 11 of the periodic table, such as Pd, Ru, Pt, Rh, Ir, Fe, Co, Ni, Cu, Ag, Re, Os, Au or any combination thereof. Another embodiment is directed to the solid support comprised of calcium fluoride, calcium oxyfluoride or calcium oxide or combination thereof, and at least one elemental metal disposed on or within said support, said elemental metal being an element of group 7, 8, 9, 10, or 11 of the periodic table, such as Pd, Ru, Pt, Rh, Ir, Fe, Co, Ni, Cu, Ag, Re, Os, Au or any combination thereof. A still further embodiment is directed to a solid support comprised of strontium fluoride, strontium oxyfluoride or strontium oxide or combination thereof, and at least one elemental metal disposed on or within said support, the elemental metal being an element of group 7, 8, 9, 10, or 11 of the periodic table, such as Pd, Ru, Pt, Rh, Ir, Fe, Co, Ni, Cu, Ag, Re, Os, Au or any combination thereof. In another embodiment, the solid support is comprised of barium fluoride, barium oxyfluoride or barium oxide or combination thereof, and at least one elemental metal disposed on or within said support, the elemental metal being an element of group 7, 8, 9, 10, or 11 of the periodic table, such as Pd, Ru, Pt, Rh, Ir, Fe, Co, Ni, Cu, Ag, Re, Os, Au or any combination thereof. The amount of elemental metal present in all of these embodiments is within the range indicted herein.

In another embodiment, the elemental metal disposed on the solid support is a metal in group 8, 9, 10 or 11 of the periodic table or a combination thereof. In still another embodiment, the elemental metal utilized is a metal of group 9 or 10 or 11 of the periodic table or combination thereof. In another aspect of the present invention, the elemental metal is Pd, Ru, Pt, Rh, Ir, Fe, Co, Ni, Cu, Ag, Re, Os, Au or any combination thereof. In a still further aspect of the present invention, the elemental metal is noble metal, which is ruthenium, rhenium, palladium, rhodium, silver, osmium, iridium, platinum, or gold or combination thereof. In another embodiment, the elemental metal is ruthenium, rhodium, palladium, osmium, iridum or platinum or combination thereof. In a still further embodiment, the elemental metal is Co, Rh, Ir, Ni, Pd, or Pt or Ru or combination thereof. In a still further embodiment, the elemental metal is Ru, Rh, Pd, Pt, or Ir or combination thereof. In still another embodiment, the elemental metal is Pd, Pt, Rh, or Ir or combination thereof. In all of the embodiments, the amount of elemental metal present on or disposed within the support is within the range described herein.

The elemental metal loading on the support ranges from about 0.01% to amount 10 wt %, based on the total weight of the elemental metal and the support. Thus, for example, the elemental element is present in any one of the following wt %: 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 However, for noble metals such as Ru, Ph, Pd, Pt, Ir, and the like, the metal loading is, in an embodiment, lower than 5 wt %, e.g., 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 wt %, while in another embodiment, the aforementioned noble metals are present in less than 1 wt %, e.g., 0.1, 0.2, 0.3, 0.4, 0.5, 0.6, 0.7, 0.8, or 0.9 wt %.

In certain embodiments, the catalyst supports are the oxides of alkaline earth metals, e.g., magnesium oxide. The alkaline earth oxides are prepared by techniques known to one of ordinary skill in the art. In one embodiment, alkaline earth metal oxides are prepared by decomposing alkaline earth metal carbonates under conditions effective to convert alkaline earth metal carbonates to corresponding oxides. For example, magnesium oxide is prepared by the methods described in *Catalysis Letters*, 70 (2000) 15-21.

In certain embodiments, the catalyst supports are the fluorides of alkaline earth metals, e.g., magnesium fluoride. The alkaline earth fluorides are prepared by techniques known to one of ordinary skill in the art. In one embodiment, alkaline earth metal fluorides are prepared by reacting alkaline earth metal oxide with sources of hydrogen fluoride such as ammonium bifluoride. For example, magnesium fluoride can be prepared by reacting magnesium oxide with ammonium bifluoride according to the chemical equation $MgO+(NH_4)HF_2 \rightarrow MgF_2+NH_3+H_2O$.

In certain embodiments, the catalyst support is the oxyfluorides of alkaline earth metals, e.g., magnesium oxyfluoride. The alkaline earth oxyfluorides are prepared by techniques known to one of ordinary skill in the art. In one embodiment, alkaline earth metal oxyfluorides are prepared through fluorinating corresponding alkaline earth metal oxides with HF under conditions effective to convert part of alkaline earth metal oxides to corresponding fluorides, and thus forming the oxyfluorides. For example, magnesium oxyfluoride can be prepared by reacting MgO with anhydrous hydrogen fluoride in a vapor phase reactor at a temperature between 300 and 600° C. for a time period of 0.5 to 20 h for different degree of fluorination.

The catalysts of the present invention are prepared by techniques known to one of ordinary skill in the art. The following description is exemplary for the preparation of the catalysts of the present invention, and should not be construed as limiting. For example, the catalyst of the present invention is prepared firstly by adding the salt of an elemental metal (e.g., Pd $(NO_3)_2$ or $PdCl_2$ for Pd) to an amount of solvent sufficient to substantially dissolve or solubilize the metal salt. The preferred solvent is one in which the metal salt is readily soluble. The choice of solvent may vary depending on the particular metal salts. Examples of solvents that can be used for the preparation of the catalyst compositions of the present invention include water, alcohols, ethers, and mixtures thereof. Useful alcohols include monohydric and polyhydric alcohols, for example, the alcohol may contain two or three hydroxyl groups and contain alkyl groups of 1-10 carbon atoms. In addition, the ether may contain one ether group or contain more than one ether group and contain 1 to 10 carbon atoms.

By alkyl, as used herein, alone or in combination with other groups, it is meant a saturated alkyl chain containing 1 to 10 carbon atoms. The alkyl group may be straight-chained or branched. Examples of alkyl group include methyl, ethyl, n-propyl, isopropyl, n-butyl, isobutyl, sec-butyl, tert-butyl, n-pentyl, isopentyl, neopentyl, n-hexyl, 2-methylpentyl, 3-methylpentyl, n-heptyl, n-octyl, n-nonyl, n-decyl, and the like.

In an embodiment, the alcohol is monohydric and the ether contains one alkoxy group, and the number of carbon atoms in the ether or alcohol being 1-6 carbon atoms. In an embodiment, the alcohol is monohydric and the ether contains one alkoxy group and the alcohol and ether each contain alkyl groups having 1 to 5 carbon atoms. Alternatively, water may be the solvent. In an embodiment, distilled water is used, while, in another embodiment, deionized water is used.

An alkaline earth metal oxide (e.g., MgO), fluoride (e.g., $MgF_2$), or oxyfluoride (e.g., $MgO_xF_y$) is then added to the solution of the elemental metal salt and then the resulting mixture is thoroughly mixed to form a slurry. After formation of the slurry, substantially all of the solvent is removed to form a solid mass of a mixture of said metal salt and said alkaline earth metal oxide (or fluoride or oxyfluoride), which is substantially solvent free. Although the solvent can be removed in one step, an aspect of the process is to drive off a portion of the solvent from the slurry to form a paste (moldable mass), followed by drying the paste to form the solid mass, i.e., powder. Any conventional technique can be used to remove the solvent. Examples of such techniques include vigorous stirring at room or elevated temperatures, evaporation, settling and decanting, centrifugation, and filtration. In an embodiment, a desired amount of solvent is evaporated using techniques known in the art to form the paste. The paste is then dried by any suitable method to form a free-flowing, substantially solvent-free powder. One method for drying includes oven drying, for example, at temperatures ranging from about 100 to about 130° C. and in another embodiment, at temperatures ranging from about 110° C. to about 120° C. Another technique for drying the paste is by spray drying. Being substantially solvent free means that less than 1 wt. %, of the solvent will remain with the powder after solvent removal/drying. In another embodiment, about 0.5 wt % or less will remain with the powder after solvent removal/drying. In another embodiment, no solvent will remain with the powder after solvent removal/drying. Upon removal of solvent, the powder will take the form of a solid mass (or powder) of a mixture of particles of the elemental metal salt and the alkaline earth metal oxide (or fluoride or oxyfluoride).

Optionally, the solid mass of the mixture of the elemental metal salt and the alkaline earth metal oxide (or fluoride or oxyfluoride) powder is then calcined for about 2 to about 8 hours. Calcination is generally carried out at a temperature ranging from about 100° C. to about 750° C., and in another embodiment, at a temperature ranging from about 200° C. to about 600° C., and in still another embodiment, at a temperature ranging from about 300° C. to about 500° C. Calcination may further optionally be carried out in the presence of an inert gas, such as nitrogen or argon, or in the presence of air or diluted air. The calcination may be carried out at a variety of pressures, such as superatmospheric, atmospheric and subatmospheric.

After calcination, the powder is optionally further grinded such that it becomes more finely-divided. The powder is further optionally pelletized in order to form pellets. If desired, excipients, such as lubricants and binders, may be added to the powder prior to pelletization.

In certain embodiments, alkaline earth metal oxide, fluoride, or oxyfluoride grains, pellets, or tablets are then added into the solution of the elemental metal salt for impregnation. After impregnation, the impregnated support is dried by any suitable methods, which include, but are not limited to oven drying, until the impregnated support is substantially dry, for example, at temperatures from about 110° C. to about 120° C. It is then calcined under nitrogen or under oxygen diluted with nitrogen, (e.g. in air) over the catalyst for about 2 to about 8 hours at a temperature ranging from about 100° C. to about 750° C., or in another embodiment, at a temperature from about 200° C. to about 600° C., and in another embodiment, at a temperature from about 300° C. to about 500° C.

The catalyst pellets are then loaded into a reactor and prior to use are pretreated. For example, they are subjected to hydrogen reduction or diluted hydrogen flow for about 2 to about 8 hours at a temperature range from about 50° C. to about 500° C., and in another embodiment, at a temperature of about 100° C. to about 400° C., and in still another embodiment, at a temperature of about 200° C. to about 300° C.

It may also be advantageous to periodically regenerate the catalyst after prolonged use while in place in the reactor. Regeneration of the catalyst may be accomplished by any means known in the art. One method is by passing oxygen or oxygen diluted with nitrogen over the catalyst at temperatures ranging from about 200° C. to about 600° C., (or in another embodiment, from about 350° C. to about 450° C.), for about 0.5 hour to about 3 days followed by reduction treatment in hydrogen or diluted hydrogen flow for about 2 to about 8 hours at a temperatures ranging from about 50° C. to about 500° C. (or in another embodiment, from about 200° C. to about 300° C.).

The catalyst produced as described above catalyzes the dehydrochlorination of a hydrochlorofluorocarbon having at least one hydrogen atom and at least one chlorine atom on adjacent carbon atoms. Table 1 lists hydrochlorofluorocarbons and their corresponding hydrofluoroolefin products.

TABLE 1

| Hydrochlorofluorocarbon | Hydrofluoroolefin |
|---|---|
| $CF_3CFClCH_3$ (244bb) | $CF_3CF=CH_2$ (1234yf) |
| $CF_3CHFCH_2Cl$ (244eb) | $CF_3CF=CH_2$ (1234yf) |
| $CF_3CH_2CHFCl$ (244fa) | $CF_3CH=CHF$ (Z/E-1234ze) |
| $CF_3CHClCH_2F$ (244db) | $CF_3CH=CHF$ (Z/E-1234ze) |
| $CF_3CFClCH_2F$ (235bb) | $CF_3CH=CHF$ (Z/E-1225ye) |
| $CF_3CHFCHFCl$ (235ea) | $CF_3CH=CHF$ (Z/E-1225ye) |
| $CF_3CH_2CF_2Cl$ (235fa) | $CF_3CH=CH_2$ (1225zc) |
| $CF_3CHClCHF_2$ (235da) | $CF_3CH=CH_2$ (1225zc) |
| $CF_3CFClCHF_2$ (226ba) | $CF_3CH=CH_2$ (1216) |

The catalyst of the present invention catalyzes the dehydrochlorination of a hydrochlorofluorocarbon having at least one hydrogen atom and at least one chlorine atom on adjacent carbon atoms. Table 2 lists hydrochlorofluorocarbons and their corresponding hydrochlorofluorocarbon products.

TABLE 2

| Hydrochlorofluorocarbon | Hydrochlorofluoroolefin olefin |
|---|---|
| $CF_3CH_2CHCl_2$ (243fa) | $CF_3CH=CHCl$ (Z/E-1233zd) |
| $CF_3CHClCH_2Cl$ (243db) | $CF_3CCl=CH_2$ (1233xf)/ $CF_3CH=CHCl$ (Z/E-1233zd) |
| $CF_3CCl_2CH_3$ (243ab) | $CF_3CCl=CH_2$ (1233xf) |
| $CF_3CHFCHCl_2$ (234ea) | $CF_3CF=CHCl$ (Z/E-1224yd) |

TABLE 2-continued

| Hydrochlorofluorocarbon | Hydrochlorofluoroolefin olefin |
|---|---|
| $CF_3CFClCH_2Cl$ (234bb) | $CF_3CF=CHCl$ (Z/E-1224yd) |
| $CF_3CHClCHCl_2$ (233da) | $CF_3CCl=CHCl$ (Z/E-1223xd)/ $CF_3CH=CCl_2$ (1223za) |
| $CF_3CCl_2CH_2Cl$ (233ab) | $CF_3CCl=CHCl$ (Z/E-1223xd) |

In certain embodiments, 1234yf is produced through the dehydrochlorination of 244bb in the presence of a catalyst of the present invention. In certain embodiments, the catalyst comprises palladium supported on magnesium oxide.

Dehydrochlorination of a hydrochlorofluorocarbon having at least one hydrogen atom and at least one chlorine atom on adjacent carbon atoms utilizing the catalyst described herein may be carried out at a temperature range of about 200° C. to about 800° C. In another embodiment, the temperature for the dehydrochlorination reaction ranges from about 300° C. to about 600° C., and in another embodiment from about 400° C. to about 500° C. in the presence of a catalyst of the present invention. It is contemplated that a variety of reaction pressures may be used, such as superatmospheric, atmospheric, and subatmospheric. In an embodiment, reactor pressures range from about 0 psig to about 200 psig, while in another embodiment from about 10 psig to about 150 psig, in another embodiment, from or from about 50 to about 100 psig.

In addition to the fluorinated olefin, the product mixture may also have unconverted hydrochlorofluorocarbon and hydrogen chloride. Enhanced or improved selectivity for the target product is an important feature of the present invention. The dehydrochlorination reaction is preferably carried out at a selectivity of at least about 50%, more preferably at least about 70%, and most preferably at least about 90%. Conversion is preferably about 10% or more and more preferably about 15% or more.

The dehydrochlorination of hydrochlorofluorocarbons may be conducted in batch operation. Alternatively, the dehydrochlorination reaction is carried out as a substantially continuous operation. Furthermore, while it is possible that the dehydrochlorination reaction may involve, in certain embodiments, a liquid phase reaction, the dehydrochlorination reaction is, in an embodiment, conducted in the vapor phase in a vapor phase reactor. In certain embodiments, the reactor is constructed from materials which are resistant to the corrosive effects of acids such as hydrogen chloride and hydrogen fluoride such as Hastalloy, Nickel, Incoloy, Inconel, and Monel. If desired, inert gases such as nitrogen or argon may be employed in the reactor during operation.

An aspect of the present invention is the preparation of 2,3,3,3-tetrafluoropropene (1234yf) from the dehydrochlorination of 1,1,1,2-tetrafluoro-2-chloropropane (244bb). More specifically, this embodiment is directed to a process of preparing of 2,3,3,3-tetrafluoroprpepne comprising dehydrochlorinating 1,1,1,2-tetrafluoro-2-chloropropane in the presence of the catalyst of the present invention, as described herein.

A further aspect of the present invention is the preparation of 2,3,3,3-tetrafluoropropene (HFO-1234yf). In certain aspects, the preparation of HFO-1234yf generally includes at least three reaction steps, as follows:

(i) $(CX_2=CCl-CH_2X$ or $CX_3-CCl=CH_2$ or $CX_3-CHCl-CH_2X)+HF \rightarrow$ 2-chloro-3,3,3-trifluoropropene (HCFO-1233xf)+HCl in a vapor phase reactor charged with a solid catalyst;

(ii) 2-chloro-3,3,3-trifluoropropene (HCFO-1233xf)+ HF→2-chloro-1,1,1,2-tetrafluoropropane (HCFC- 244bb) in a liquid phase reactor charged with a liquid hydrofluorination catalyst; and (iii)₂-chloro-1,1,1,2-tetrafluoropropane (HCFC-244bb) →2,3,3,3-tetrafluoropropene (HFO-1234yo in a vapor phase reactor, wherein X is independently selected from F, Cl, Br, and I, provided that at least one X is not fluorine.

Generally speaking, the starting material of the first reaction step may be represented by one or more chlorinated compounds according to Formulas I, II, and/or III:

CX₂=CCl—CH₂X                    (Formula I)

CX₃—CCl=CH₂                     (Formula (II)

CX₃—CHCl—CH₂X                   (Formula III)

wherein X is independently selected from F, Cl, Br, and I, provided that at least one X is not fluorine. In certain embodiments, these compounds contain at least one chlorine, a majority of X is chlorine, or all X is chlorine.

In the first step, such starting materials (which, in certain embodiments includes 1,1,2,3-tetrachloropropene (1230xa) and/or 1,1,1,2,3-pentachloropropane (HCC-240 db)) is reacted with anhydrous HF in a first vapor phase reactor (fluorination reactor) to produce a mixture of at least HCFO-1233xf (2-chloro-3,3,3-trifluoropropene) and HCl. The reaction can be carried out at a temperature of about 200-400° C. and a pressure of about 0-200 psig. The effluent stream exiting the vapor phase reactor may optionally comprise additional components, such as un-reacted HF, heavy intermediates, HCFC-244bb, HFC-245cb (1,1,1,2,2-pentafluoropropane), or the like.

This reaction may be conducted in any reactor suitable for a vapor phase fluorination reaction. The reactor may be constructed from materials which are resistant to the corrosive effects of hydrogen fluoride and catalyst such as Hastalloy, Inconel, Monel. In case of a vapor phase process, the reactor is filled with a vapor phase fluorination catalyst. Any fluorination catalysts known in the art may be used in this process. Suitable catalysts include, but are not limited to, chromium, aluminum, cobalt, manganese, nickel and iron oxides, hydroxides, halides, oxyhalides, inorganic salts thereof and their mixtures, any of which may be optionally halogenated. Combinations of catalysts suitable for the present invention nonexclusively include $Cr_2O_3$, $FeCl_3/C$, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Chromium oxide/aluminum oxide catalysts are described in U.S. Pat. No. 5,155,082, the contents of which are incorporated herein by reference. In another embodiment, the catalyst is a chromium (III) oxides such as crystalline chromium oxide or amorphous chromium oxide, and still another embodiment, the catalyst is amorphous chromium oxide. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to catalyze the reaction.

This first step of the reaction is not necessarily limited to a vapor phase reaction, as described above, but may also be performed using a liquid phase reaction or a combination of liquid and vapor phases, such as that disclosed in U.S. Published Patent Application No. 20070197842, the contents of which are incorporated herein by reference. It is also contemplated that the reaction can be carried out batch wise, continuously, or a combination of these. For embodiments in which the reaction comprises a liquid phase reaction, the reaction can be catalytic or non-catalytic. Lewis acid catalysts, such as metal-halide catalysts, including antimony halides, tin halides, thallium halides, iron halides, and combinations of two or more of these, may be employed. In certain embodiments, metal chlorides and metal fluorides are employed, including, but not limited to, $SbCl_5$, $SbCl_3$, $SbF_5$, $SnCl_4$, $TiCl_4$, $FeCl_3$ and combinations of two or more of these.

The effluent from the reactor may be optionally processed to achieve desired degrees of separation and/or other processing. By way of non-limiting example, the product effluent may contain one or more impurities, such as, HCl, unconverted reactants, and/or other by-products. These products may be removed using standard methods known or otherwise discussed herein. HCl, for example, can be recovered by conventional distillation, or using water or caustic scrubbers, as discussed in greater detail below, and the unreacted starting reagents isolated and recycled.

In the second step of the process for forming 2,3,3,3-tetrafluoropropene, HCFO-1233xf, is converted to HCFC-244bb. In one embodiment, this step may be performed in the liquid phase in a liquid phase reactor, which may be TFE or PFA-lined. Such a process may be performed in a temperature range of about 70-120° C. and about 50-120 psig.

Any liquid phase fluorination catalyst may be used in the invention. A non-exhaustive list includes Lewis acids, transition metal halides, transition metal oxides, Group IVb metal halides, a Group Vb metal halides, or combinations thereof. Non-exclusive examples of liquid phase fluorination catalysts are antimony halide, tin halide, tantalum halide, titanium halide, niobium halide, molybdenum halide, iron halide, fluorinated chrome halide, fluorinated chrome oxide or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof. For example, a specific non-exclusive example of a liquid phase fluorination catalysts is antimony pentachloride.

These catalysts can be readily regenerated by any means known in the art if they become deactivated. One suitable method of regenerating the catalyst involves passing a stream of chlorine through the catalyst. For example, from about 0.002 to about 0.2 lb per hour of chlorine can be added to the liquid phase reaction for every pound of liquid phase fluorination catalyst. This may be done, for example, for from about 1 to about 2 hours or continuously at a temperature of from about 65° C. to about 100° C.

This second step of the reaction is not necessarily limited to a liquid phase reaction and may also be performed using a vapor phase reaction or a combination of liquid and vapor phases, such as that disclosed in U.S. Published Patent Application No. 20070197842, the contents of which are incorporated herein by reference. To this end, the HCFO-1233xf containing feed stream is preheated to a temperature of from about 50° C. to about 400° C., and is contacted with a catalyst and fluorinating agent. Catalysts may include standard vapor phase agents used for such a reaction and fluorinating agents may include those generally known in the art, such as, but not limited to, hydrogen fluoride.

In the third step of HFO-1234yf production, HCFC-244bb is, in one embodiment, fed to a second vapor phase reactor (dehydrochlorination reactor) to be dehydrochlorinated to make the desired product 2,3,3,3-tetrafluoropropene (HFO- 1234yf). The dehydrochlorination is conducted in accordance with the description herein.

It is to be noted that the effluent from the dehydrochlorination reactor in the aforementioned reaction or in any of the other dehydrochlorination may be processed to achieve desired degrees of separation and/or other processing. Besides HFO-1234yf produced, the effluent generally contains HCl, unconverted HCFC-244bb, and HCFO-1233xf (which is mainly carried over from the previous step of HCFO-1233xf hydrofluorination). Optionally, HCl is then recovered from the result of the dehydrochlorination reaction. Recovery of HCl is conducted by conventional distillation where it is removed from the distillate. Alternatively, HCl can be recovered or removed by using water or caustic scrubbers. When a water extractor is used, HCl is removed as an aqueous solution. When a caustic solution is used, HCl is removed from system as a chloride salt in aqueous solution. After the recovery or removal of HCl, the organic stream may be sent to a distillation column for separation. HFO-1234yf, collected from the overhead of the column, may be sent to another column for further purification, while a fraction of the mixture of HCFO-1233xf and HCFC-244bb, accumulated in the reboiler, may be sent back to the dehydrochlorination reactor for the recycle of HCFC-244bb, and the rest to the HCFO-1233xf hydrofluorination reactor for the recycle of HCFO-1233xf.

In vapor-phase 244bb dehydrochlorination, 244bb feed, which can be formed from 1233xf hydrofluorination as described in US 20090240090, the contents of which are incorporated herein by reference, is fed continuously to a vaporizer and the vaporized feed to a reactor. Due to incomplete conversion of 1233xf and its close boiling point to 244bb as well as the formation of azeotrope or azeotrope-like composition of 244bb and 1233xf under certain conditions, the separation of these two compounds is difficult. For this reason, the 244bb feed generally contains certain amount of 1233xf. The dehydrochlorination reaction may be carried out under conditions to attain a 244bb conversion of about 5% or higher, about 20% or higher, or about 30% or higher. The reaction may be carried out at a temperature in the range of from about 200° C. to about 800° C., in one embodiment, or from about 300° C. to about 600° C., in another embodiment or from about 400° C. to about 500° C. in the third embodiment; the reactor pressure may be in the range of from about 0 psig to about 200 psig, in one embodiment, from about 10 psig to about 150 psig in a second embodiment, or, in a third embodiment, from about 50 to about 100 psig.

The present process using the catalyst of the present invention is very efficient. It is more efficient than if an unsupported mixture of the elemental metal and the alkaline earth metal fluoride, oxyfluoride or oxide were used. Unlike the use of the nonsupported catalyst, the present process does not require a high loading of metal. In addition, using the supported catalyst of the present invention, the reactants are exposed to a greater surface area and thus can react more quickly utilizing the catalyst system of the present invention than if an equal amount of non-supported catalyst comprised of the same components in the same proportions were used. Enhanced and improved selectivity for the formation of the fluoroolefin also results from the use of the catalyst system of the present application. The selectivity of the dehydrochlorination reaction utilizing the catalyst of the present invention is about 90% or more and can be as high as 95% or more. Conversion utilizing the catalyst of the present invention is about 10% or more, in an embodiment is about 15% or more.

The following non-limiting examples further illustrate the present invention.

EXAMPLES

Example 1

In Example 1, a 1 wt % Pd/MgO catalyst was prepared by (a) dissolving 0.76 g of $Pd(NO_3)_2 \cdot 2H_2O$ in 40 ml of D.I. water in a beaker to form a $Pd(NO_3)_2$ aqueous solution; (b) adding 30.00 grams of a MgO granules in the $Pd(NO_3)_2$ solution; (c) stirring periodically with a glass rod to help mix well and driving off water until the pellets could move freely; (d) drying the $Pd(NO_3)_2$-doped MgO granules in an oven at 110° C. for 4 h; (e) calcining the dried $Pd(NO_3)_2$-doped MgO granules in $N_2$ flow for 4 h at a temperature of 400° C.

20 cc of the calcined catalyst granules was loaded into a ¾-inch Monel reactor and was reduced in $H_2$ for 2 h at 300° C. prior to use.

Example 2

The 1 wt % Pd/MgO catalyst prepared in Example 1 was used for 244bb dehydrochlorination. The reactor was heated to 450° C. in nitrogen flow. After the temperature was stabilized, a mixture of 99.1%244bb/0.4%1233xf mole percent was then passed through the catalyst bed at a rate of 6 grams/hour (g/h). The reactor pressure was set at 1 atm. As shown in Table 3, the 1 wt % Pd/MgO catalyst provided a 244bb conversion of about 18% and a 1234yf selectivity of about 97% after 13.5 h on stream and remained stable in the next 12 hours.

TABLE 3

| Catalyst | Time-on-stream (h) | 244bb conv., (%) | Selectivity, % | | |
|---|---|---|---|---|---|
| | | | 1234yf | 1233xf | others |
| 1 wt % Pd/MgO | 3.5 | 22.2 | 67.8 | 12.7 | 19.4 |
| | 13.5 | 17.9 | 97.1 | 0.9 | 2.0 |
| | 17.5 | 18.4 | 97.8 | 0.0 | 2.2 |
| | 21.5 | 18.3 | 97.8 | 0.0 | 2.2 |
| | 25.5 | 17.6 | 96.7 | 0.6 | 2.7 |

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A catalyst comprising (a) a solid support comprising an alkaline earth metal oxide or oxyfluoride or combination thereof and (b) at least one elemental metal disposed on or within said support, wherein said elemental metal is present in an amount ranging from about 0.01 to about 10 weight percent based upon the total weight of the elemental metal and support, said elemental metal being one or more metals from Groups 7, 8, 9, 10, or 11 of the periodic table.

2. The catalyst according to claim 1 wherein the solid support comprises an alkaline earth oxide.

3. The catalyst according to claim 2 wherein the alkaline earth metal is magnesium, calcium, strontium or barium.

4. The catalyst according to claim 2 wherein the alkaline earth metal is magnesium.

5. The catalyst according to claim 1 wherein the elemental metal is an element of groups 8, 9, 10, or 11 of the periodic table.

6. The catalyst according to claim 1 wherein the elemental metal is an element of groups 9, 10, or 11 of the periodic table.

7. The catalyst according to claim 1, wherein the elemental metal is Pd, Ru, Pt, Rh, Ir, Fe, Co, Ni, Cu, Ag, Re, Os, Au or combination thereof.

8. The catalyst according to claim 7 wherein the elemental metal is Co, Rh, Ni, Pd, Pt or Ir or combination thereof.

9. The catalyst according to claim 7 wherein the elemental metal is Ru, Rh, Pd, Pt, or Ir or combination thereof.

10. The catalyst according to claim 9 wherein the elemental metal is present on or within said support in an amount ranging from about 0.1% to about 5% by weight.

11. The catalyst according to claim 10 wherein the elemental metal is present on or within said support in an amount ranging from about 0.1% to about 0.9 wt %.

12. A process for preparing a fluoroolefin from a hydrochlorofluorocarbon having at least one hydrogen atom and at least one chlorine atom on adjacent carbon atoms comprising dehydrochlorinating said hydrochlorofluorocarbon in the presence of a catalyst, said catalyst comprising (a) a solid support comprising an alkaline earth metal fluoride, oxide or oxyfluoride or combination thereof, and (b) at least one elemental metal disposed on or within said support, wherein said elemental metal is present in an amount from about 0.01 to about 10 weight percent based upon the total weight of the elemental metal and said solid support, said elemental metal being one or more metals from Groups 7, 8, 9, 10, or 11 of the periodic table or combination thereof.

13. The process according to claim 12 wherein the solid support comprises an alkaline earth oxide.

14. The process according to claim 12 wherein the alkaline earth metal is magnesium, calcium, strontium or barium.

15. The process according to claim 12 wherein the alkaline earth metal is magnesium.

16. The process according to claim 12 wherein the solid support comprises magnesium oxide.

17. The process according to claim 12, wherein the elemental metal is an element of groups 8, 9, 10, or 11 of the periodic table.

18. The process according to claim 17 wherein the elemental metal is an element of groups 9, 10, or 11 of the periodic table.

19. The process according to claim 17 elemental metal is elemental metal is wherein the elemental metal is Pd, Ru, Pt, Rh, Ir, Fe, Co, Ni, Cu, Ag, Os, Au or combination thereof.

20. The process according to claim 19 wherein the elemental metal is Co, RhNi, Pd, Pt or Ir or combination thereof.

21. The process according to claim 19 wherein the elemental metal is Ru, Rh, Pd, Pt, or Ir or combination thereof.

22. The process according to claim 21 wherein the elemental metal is present on or within said support in an amount ranging from about 0.1% to about 5% by weight.

23. The process according to claim 21 the elemental metal is present on or within said support in an amount ranging from about 0.1% to about 0.9 wt %.

24. The process according to claim 12 wherein the dehydrochlorinating takes place in the vapor phase and is conducted at a temperature ranging from about 200° C. to about 800° C.

25. The process according to claim 24 where the temperature of the dehydrochlorination reaction ranges from about 300° C. to about 600° C.

26. The process according to claim 12 where the dehydrochlorination reaction takes place in the vapor phase and is conducted at a pressure ranging from about 0 psig to about 200 psig.

27. The process according to claim 26 wherein the dehydrochlorination reaction is conducted at a pressure of about 10 psig to about 150 psig.

28. The process according to claim 12 wherein the hydrochlorofluorocarbon is 1,1,1,2-tetrafluoro-2-chloropropane and the fluoroolefin is 2,3,3,3-tetrafluoropropene.

29. The process according to claim 12 wherein the hydrochlorofluorocarbon is $CF_3CHFCH_2Cl$ and the fluoroolefin is $CF_3CF=CH_2$.

30. The process according to claim 12 wherein the hydrochlorofluorocarbon is $CF_3CH_2CHFCl$ and the fluoroolefin is $CF_3CH=CHF$ (Z/E).

31. The process according to claim 12 wherein the hydrochlorofluorocarbon is $CF_3CHClCH_2F$ and the fluoroolefin is $CF_3CH=CHF$ (Z/E).

32. The process according to claim 12 wherein the hydrochlorofluorocarbon is $CF_3CFClCH_2F$ and the fluoroolefin is $CF_3CF=CHF$ (Z/E).

33. The process according to claim 12 wherein the hydrochlorofluorocarbon is $CF_3CHFCHFCl$ and the fluoroolefin is $CF_3CF=CHF/(Z/E)$.

34. The process according to claim 12 wherein the hydrochlorofluorocarbon is $CF_3CH_2CF_2Cl$ and the fluoroolefin is $CF_3CH=CF_2$.

35. The process according to claim 12 wherein the hydrochlorofluorocarbon is $CF_3CHClCHF_2$ and the fluoroolefin is $CF_3CH=CF_2$.

36. The process according to claim 12 wherein the hydrochlorofluorocarbon is $CF_3CFClCHF_2$ and the fluoroolefin is $CF_3CF=CF_2$.

37. The process according to claim 12 wherein the hydrochlorofluorocarbon is $CF_3CH_2CHCl_2$ and the fluoroolefin is $CF_3CH=CHCl$ (Z/E).

38. The process according to claim 12 wherein the hydrochlorofluorocarbon is $CF_3CHClCH_2Cl$ and the fluoroolefin is $CF_3CCl=CH_2$ or $CF_3CH=CHCl$ (Z/E).

39. The process according to claim 12 wherein the hydrochlorofluorocarbon is $CF_3CCl_2CH_3$ and the fluoroolefin is $CF_3CCl=CH_2$.

40. The process according to claim 12 wherein the hydrochlorofluorocarbon is $CF_3CHFCHCl_2$ and the fluoroolefin is $CF_3CF=CHCl$ (Z/E).

41. The process according to claim 12 wherein the hydrochlorofluorocarbon is $CF_3CHClCHCl_2$ (233da) and the fluoroolefin is $CF_3CCl=CHCl$ (Z/E) or $CF_3CH=CCl_2$.

42. The process according to claim 12 wherein the hydrochlorofluorocarbon is $CF_3CCl_2CH_2Cl$ and the fluoroolefin is $CF_3CCl=CHCl$ (Z/E).

43. A process for preparing 2,3,3,3-tetrafluoropropene comprising:
 (i) providing a starting composition comprising a compound of Formulae I, II, or III:

$$CX_2=CCl-CH_2X \qquad (I);$$

$$CX_3-CCl=CH_2 \qquad (II); \text{ or}$$

$$CX_3-CHCl-CH_2X \qquad (III)$$

wherein X is independently selected from F, Cl, Br, and I, provided that at least one X is not fluorine;
 (ii) contacting the starting composition with a first fluorinating agent to produce a first intermediate composition comprising 2-chloro-3,3,3-trifluoropropene and a first chlorine-containing byproduct;
 (iii) contacting the first intermediate composition with a second fluorinating agent to produce a second intermediate composition comprising 2-chloro-1,1,1,2-tetrafluoropropane; and (iv) dehydrochlorinating in the presence of a catalyst, at least a portion of the second intermediate composition comprising 2-chloro-1,1,1,2-tetrafluoropropane to produce a reaction product comprising 2,3,3,3-tetrafluoropropene, said catalyst comprising (a) a solid support comprising an alkaline earth metal fluoride, oxide or oxyfluoride or combination thereof, and (b) at least one elemental metal disposed on or within said support, wherein said elemental metal is present in an amount ranging from about 0.01 to about 10 weight percent based upon the total weight of the metal and support, said elemental metal being one or more metals from Groups 7, 8, 9, 10, or 11 of the periodic table.

44. The process according to claim 43 wherein the solid support comprises an alkaline earth metal oxide.

45. The process according to claim 43 wherein the alkaline earth metal is magnesium, calcium, strontium or barium.

46. The process according to claim 43 wherein the alkaline earth metal is magnesium.

47. The process according to claim 43 wherein the elemental metal is Pd, Ru, Pt, Rh, Ir, Fe, Co, Ni, Cu, Ag, Re, Os, Au or combination thereof.

* * * * *